United States Patent
Litovsky

(10) Patent No.: US 6,584,440 B2
(45) Date of Patent: Jun. 24, 2003

(54) METHOD AND SYSTEM FOR RAPID AND RELIABLE TESTING OF SPEECH INTELLIGIBILITY IN CHILDREN

(75) Inventor: Ruth Y. Litovsky, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/067,163

(22) Filed: Feb. 4, 2002

(65) Prior Publication Data

US 2002/0107692 A1 Aug. 8, 2002

Related U.S. Application Data

(60) Provisional application No. 60/266,167, filed on Feb. 2, 2001.

(51) Int. Cl.[7] .............................. G09B 5/06; G09B 19/04
(52) U.S. Cl. ........................ 704/271; 434/185; 434/322
(58) Field of Search ................................. 704/270, 271; 434/180, 185, 322, 323; 381/60

(56) References Cited

U.S. PATENT DOCUMENTS

| | | | |
|---|---|---|---|
| 3,745,674 A | | 7/1973 | Thompson et al. |
| 4,224,468 A | | 9/1980 | Calder, Jr. |
| 4,862,505 A | | 8/1989 | Keith et al. |
| 5,303,327 A | | 4/1994 | Sturner et al. |
| 5,428,998 A | * | 7/1995 | Downs ........................ 73/585 |
| 5,870,481 A | * | 2/1999 | Dymond et al. .............. 381/17 |
| 6,026,361 A | | 2/2000 | Hura |
| 6,056,549 A | * | 5/2000 | Fletcher ...................... 283/46 |
| 6,109,107 A | | 8/2000 | Wright et al. |
| 6,167,138 A | * | 12/2000 | Shennib ..................... 381/23.1 |
| 6,206,700 B1 | * | 3/2001 | Brown et al. .......... 340/825.19 |
| 6,302,697 B1 | * | 10/2001 | Tallal et al. ................. 434/118 |
| 6,319,207 B1 | * | 11/2001 | Naidoo ........................ 600/300 |

* cited by examiner

Primary Examiner—Marsha D. Banks-Harold
Assistant Examiner—Martin Lerner
(74) Attorney, Agent, or Firm—Patricia Smith King

(57) ABSTRACT

A method and system for testing the speech intelligibility of a child comprises providing a set of target sounds as words in the presence and absence of competing sound(s) of a variety of types so as to enable an analysis of the aspects of competing sounds and their respective effects on the speech intelligibility of a child. Locations at which competing sound(s) is provided is varied to enable an evaluation of its effect on the spatial release from masking. The target words used in the test are first determined to be within the vocabulary of the child. The child is required to respond to the target word by selecting a picture representation of the target word from among several picture choices, thus providing an interactive aspect to the test. There may optionally be provided a positive or a negative reinforcement. The sound level at which the target words are presented may vary adaptively according to the child's responses, the change in sound level being determined by a set of rules. The test is repeated over several target words and under a variety of types and locations of competing sounds and the child's responses recorded in a results database. The results are available for further analysis by a user to produce customized output. A computerized system is disclosed that enables the provisioning of the test in a controlled manner, analysis of the data and further engagement the child.

21 Claims, 4 Drawing Sheets

METHOD AND SYSTEM FOR RAPID AND RELIABLE TESTING OF SPEECH INTELLIGIBILITY IN CHILDREN

CROSS-REFERENCES

This application is entitled to the benefit of U.S. Provisional Patent Application Ser. No. 60/266,167, filed Feb. 2, 2001 entitled "Hearing test" by inventor Ruth Y. Litovsky, and is incorporated herein by this reference and which is not admitted to be prior art with respect to the present invention by its mention in this Cross-references Section or in the Background Section.

STATEMENT REGARDING FEDERALLY SPONSORED RESEARCH OR DEVELOPMENT

This invention was made with United States government support awarded by the following agencies: NIH DC0010.

BACKGROUND

A person's ability to hear and understand speech may have a profound impact on their performance in life. Detection and evaluation of speech intelligibility problems can greatly aid in their treatment, thereby increasing a person's capability to understand speakers in their environment. Speech intelligibility tests are essential to detecting and evaluating problems in distinguishing speech from other sounds. Of particular importance are tests designed for children so that early detection of speech intelligibility problems is possible.

There are several aspects to hearing that must be measured in order to properly evaluate a person's ability to distinguish speech. One aspect is the extent to which a person is able to hear what one person is saying in the presence of competing voices or other sounds, the so called "cocktail party problem." In children, this problem is likely to surface in classroom situations, the very places where children must be able to distinguish the speech of a teacher from the general noise of the classroom, in order to perform well.

For this reason, there is a need for a test to determine the effect(s) of the presence of competing sounds, their types and locations on speech intelligibility in children. Such information is useful in evaluating a base level of speech intelligibility of a child and in analyzing what treatment(s), if any, may improve the child's ability to hear. For example, would a hearing aid or cochlear implant benefit the child more? If a child is listening to a target speaker, is there less of a masking effect of competing sounds when they are removed spatially from the speaker (i.e. spatial release from masking or the increased speech intelligibility observed when the target and competing sounds are spatially separated)? If so, what environmental conditions, such as where the child sits in a classroom, might maximize the child's ability to hear? Is a child's spatial release from masking aided by his or her binaural hearing (i.e., the ability to hear with two ears simultaneously and to extract information from the environment that relies on comparing inputs to the two ears), as with adults?

To enable these evaluations, a speech intelligibility test must be able to measure the extent to which spatial release from masking can occur in a realistic environment such as a classroom, thereby providing a more realistic means of predicting a child's performance in the classroom. Furthermore, because children have notoriously short attention spans, a speech intelligibility test must be able to gain reliable results rapidly while engaging the attention of the child.

Prior studies and tests have focused on adult auditory abilities, and to a limited extent, infant auditory abilities, but little is known regarding the auditory abilities of children. For this reason, the ability of children to process complex acoustic inputs and resolve competition for perception and localization between target sources and interfering competing sounds is not known.

Several studies have suggested that one of the primary differences between adults and children is in their speech intelligibility in complex acoustic situations. But prior tests designed specifically for children, are few and insufficient to the task of (1) engaging children, who generally have short attention spans, to enable a tester to determine what auditory factors (including both type and location of competing sound) are contributing to the child's speech intelligibility level; (2) simulating a child's average noisy classroom environment to enable evaluation under realistic circumstances; (3) providing a clinically reliable test able to link the child's environmental experience to the audiology clinic.

For the foregoing reasons, there is a need for a method and system for clinically testing speech intelligibility in children in the presence of competing sounds that vary by type and location. The test must be fast and engaging and able to provide a reliable measure of a child's speech intelligibility and the extent to which spatial release from masking can occur in a realistic environment, which may include either a quiet room or a noisy room such as a classroom, thereby providing a more realistic means than a simple hearing test of predicting a child's performance in the classroom and information that can be used to tailor a child's treatment.

SUMMARY

The present invention is directed to satisfying this need by providing a method and system for rapid and reliable measurement of a child's speech intelligibility so as to enable measurement of an interference and masking effect of the competing sound by its type and location on an ability of the child to hear the target and to spatially segregate sounds using binaural hearing, that is, the degree to which masking and spatial release from masking can occur given characteristics of the type of competing sound and its location relative to the child and to the target, the measurements informing treatment options to improve the child's speech intelligibility in realistic complex environments.

In one version, the method for testing speech intelligibility of a child comprises providing a set of target words for presenting to the child from an auditory target located in front of the child; selecting the set of target words from a plurality of words by determining which of said plurality of words are within a vocabulary of the child, whereby the set of target words comprises only words familiar to the child; providing a set of picture representations of each of said target words for visually presenting to the child; providing a set of competing sounds of an at least one type of competing sound, including speech, speech-shaped noise, time-reversed speech and modulated speech-shaped noise; specifying a sound level at which a target word is presented so as to ensure hearing by the child in the absence of any of the competing sounds; presenting one of the target words to the child at the sound level; presenting a subset of the picture representations to the child of which one matches the presented target word, the child then responding to the presentation by choosing which picture matches the target word, and recording the child's response; and, repeating the presenting the target word step while furthermore simultaneously presenting the selected type of the competing sound at a location proximate the target and repeating the presenting the picture representations step, over all of the competing sounds selected; and, repeating the presenting the target word step while furthermore simultaneously presenting the selected type of competing sound at a location at a distance away from both the target and the child and repeating the presenting the picture representations step, over all of the competing sounds selected.

In another version, the method further comprises changing the sound level at which the target word is presented adaptively, according to the child's response; changing the sound level comprising determining a direction and an amount of an initial step size by which to change the sound level so as to adapt the change in current sound level to the child's response, the determination being governed by a set of rules.

In another version of the method, presenting the subset of picture representations comprises presenting the pictures on a computer screen at the location of the child; the child choosing which of the subset of pictures matches the target word by pointing a cursor to the chosen picture by moving a mouse and clicking the mouse when the cursor is in position at the chosen picture.

In another version, an apparatus is provided having means for performing one or more of the processes described above.

In another aspect, a program storage device, readable by a machine, tangibly embodying a program of instructions executable by the machine is provided to perform one or more of the processes described above.

In another aspect, an article having a computer-usable medium has computer-readable program code embodied in the medium for performing one or more of the processes described above.

In another aspect, a computer program product is provided to perform one or more of the processes described above.

The reader is advised that this summary is not meant to be exhaustive. These and other features and aspects of the method and system will become better understood with reference to the following description, accompanying drawings, and appended claims.

Several objects and advantages of the present invention are to provide:
a) a method and system for testing speech intelligibility of children in such as way as to link the child's normal environmental noise experience to the audiology clinic;
b) a rapid and reliable method and system for testing the speech intelligibility of a child that is adapted to engage children so as to enable a tester to determine what auditory factors are contributing to the child's speech intelligibility level;
c) a method and system for simulating a child's normal classroom environment by providing a variety of types of competing noises so as to determine their effect(s) on the speech intelligibility of the child;
d) a method and system for testing the effects of location of competing noises relative to a target word source and the child so as to determine the spatial release from masking potential of said location; and,
e) a system for computerizing the method so as to enable a clinical user to more accurately control the presentation of sounds, the storage and analysis of results, and by which the child may interactively make choices and receive reinforcement.

BRIEF DESCRIPTION OF DRAWINGS

For a better understanding of the present invention, reference may be made to the accompanying drawings, in which.

DESCRIPTION

Figure 1:
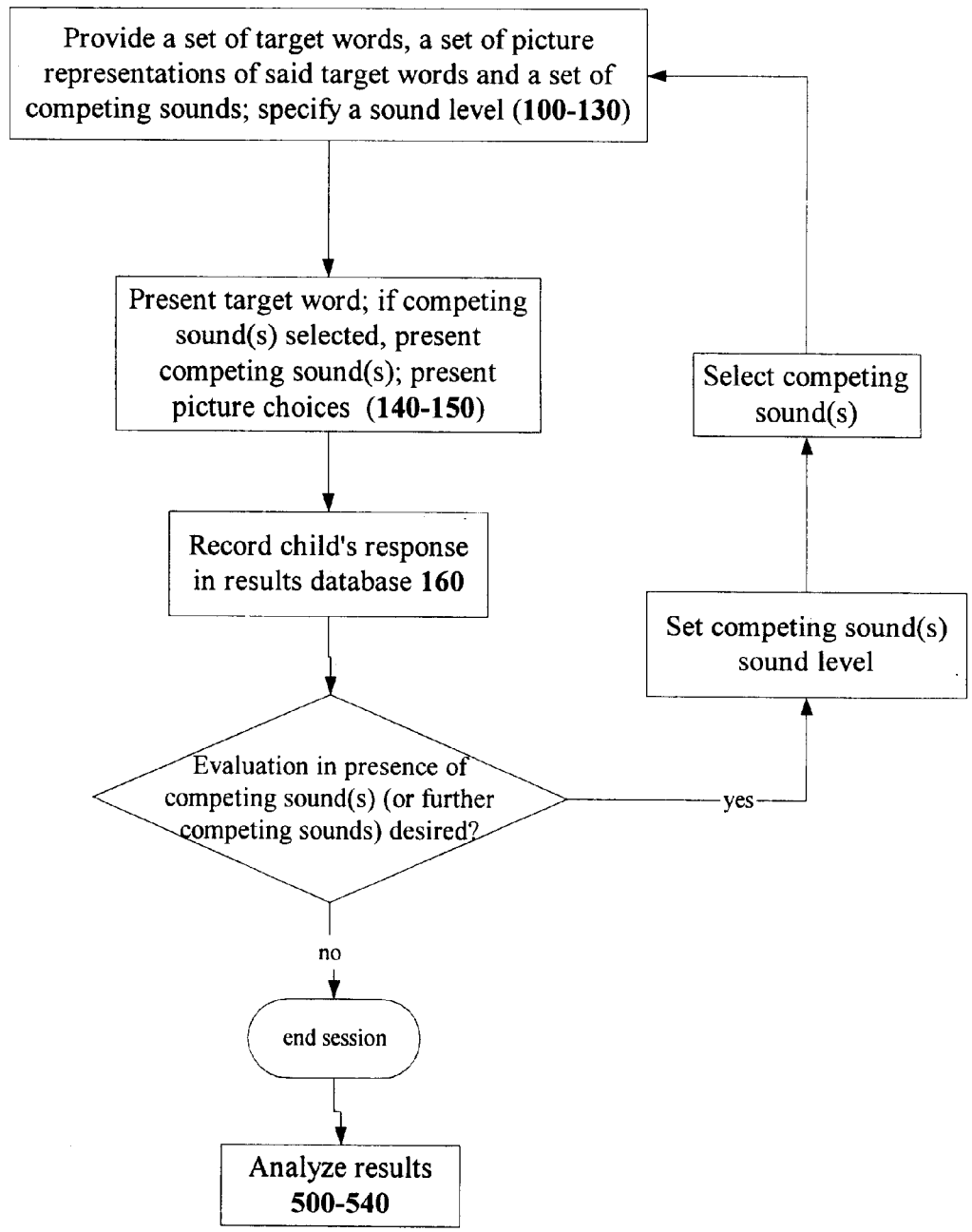
FIG. 1 shows a schematic diagram depicting the basic steps in a version of the method.

Referring now specifically to the figures, in which identical or similar parts are designated by the same reference numerals throughout, a detailed description of the present invention is given. It should be understood that the following detailed description relates to the best presently known embodiment of the invention. However, the present invention can assume numerous other embodiments, as will become apparent to those skilled in the art, without departing from the appended claims. For example, the method and system of the present invention may be applied to testing hearing in subjects other than children.

It should also be understood that, while the methods disclosed herein may be described and shown with reference to particular steps performed in a particular order, these steps may be combined, sub-divided, or re-ordered to form an equivalent method without departing from the teachings of the present invention. Accordingly, unless specifically indicated herein, the order and grouping of the steps is not a limitation of the present invention.

Detailed Description—Method

The method of the present invention enables rapid and reliable measurement of a child's hearing ability in the absence and presence of competing noise(s). A description of the general steps is given below and an example of a particular version of their use is given in the section, How to use the invention below.

Providing a set of target words 100. A set of target words is provided as part of an inputs database 390 (and may be augmented by user input 395) as sound files. Alternatively, the target words may be provided on audiotape, compact disc or the like as user input 395.

The target words are used for presentation to the child from an auditory target located in front of and at a distance from the child. The auditory target generally comprises an audio speaker 220 (see FIG. 3). The target words may be of a variety of kinds including single syllable words, multiple syllable words including children's spondees (i.e. words made up of two words like airplane and barnyard), or other types of words.

Familiarization procedure. From the initial set of target words, words in the vocabulary of the child are chosen for use in testing the child's hearing. To determine which words are familiar to the child a familiarization procedure is conducted (see below under the How invention is used section). By performing this step, only words familiar to the child are used in the child's speech intelligibility test and this helps to eliminate an effect of guessing by the child when the child hears a word they do not understand.

As mentioned below, the picture representations of target words may be in hardcopy in the form of a book of pictures or the like. When pictures are provided in this manner, all target words are included and the familiarization procedure ensures that each child is thoroughly familiar with all target words.

Providing a set of target word pictures 110. A set of picture representations of each of the target words is also provided in the inputs database 390 (and may be augmented by user input 395) as graphics files. The pictures symbolize what each target word means.

Alternatively, the picture representations may be in hardcopy in the form of a book of pictures or the like and presented to the child manually.

Providing a set of types of competing sounds 120. The speech intelligibility test is conducted both in silent conditions and in conditions where other sounds are simultaneously presented with the target word, that compete with the target sound. These competing sounds are provided in a variety of types to enable analysis of what characteristics of the competing sounds are affecting the hearing ability of the child. A set of various types of competing sounds is provided in the inputs database 390 (and may be augmented by user input 395) as sound files. Alternatively, the competing sounds may be provided on audiotape, compact disc or the like as user input 395. Several types of competing sounds may be provided including noise, speech, speech-shaped noise, time-reversed speech, temporally modulated speech-shaped noise, or any number of user-specified sounds.

The speech-type competing sounds may be in the form of sentences. For example, digitized sentences from the Harvard IEEE list or other sources may be used. Examples of typical competing sound sentences are, "Glue the sheet to the dark blue background," "Two blue fish swam in the tank," and, "The meal was cooked before the bell rang."

Specifying a sound level and calibrating 130. A sound level (in decibels at sound pressure level, db SPL) is specified at which a target word is presented so as to ensure hearing by the child in the absence of any of the competing sounds. Related to this specification is assuring that a target word is actually presented at the site of the child by calibrating the presentation of the target word sound. A sound meter may be employed to read the sound level at the child's station 210 (see FIG. 3) at the approximate location of the child's head. Once properly calibrated, a user may ensure that the target word presented by the target audio speaker 220 reaches the child at the proper sound level. Proper calibration also ensures that if a user opts to vary the sound level in response to the child's responses (see below at Adapting sound level given child's response 170), the step sizes by which the sound level is changed will be accurately implemented.

Overview of testing procedure. The speech intelligibility test generally involves a one-interval multiple-alternative-forced-choice discrimination procedure. On each trial, one of the provided target words is presented aurally, and the child is asked to identify the picture representation matching that target word from a selection of multiple picture representations, only one of which matches the presented target word. The prior familiarization procedure ensures that the target word is familiar to the child.

Each trial is run under a variety of conditions. The conditions may generally include (1) quiet where the target words are presented from a location in front of and at a distance from the child with no competing sounds present; (2) target/competitor overlap where a competing sound source(s) is also presented and it is presented from a location in front of and at a distance from the child as well; and, (3) target/competitor separated where a competing source(s) is presented as in (2) but from a location(s) other than the location of the target (e.g. at location(s) of 90 degrees to the right and/or left of the subject). In conditions (2) and (3) either or two competitor sounds may be present. From (3) where the competing source is placed to the right or left of the subject, the results may indicate the effects of the child's binaural hearing ability on the ability to effectively mask a competing sound by locating it to the right and/or left of the target source.

While the competing sound(s) is presented, a leading phrase such as, "point to the picture of the . . . " precedes the presentation of the target word. After the target word is presented, the child is asked to indicate which picture representation matches the target word spoken. An adaptive variation of sound level (see 170 below) may optionally be used to vary the sound level of the target word, such that correct responses result in sound level decrement and incorrect responses result in sound level increment.

Presenting the target words and picture choices 140. A target word is presented to the child at the target audio speaker 220. When this occurs, a subset of the picture representations of the target words appears at the child's station 210 on the screen 212 (see FIG. 3). The child is then asked to respond by choosing which of the subset of pictures presented matches the target word. The child may make the selection by moving a cursor on the screen with a mouse 214 or may touch the chosen picture on the screen in the case of a touch screen display, or by some other means.

Once the child makes his or her choice, the child's response is recorded 160. If the answer is correct, a positive reinforcement screen may be presented to the child showing an amusing animation of some sort, for example. Alternatively, no reinforcement may be given. If the answer is incorrect, there may optionally be no response made, or a user may specify some sort of reinforcement response that may be either positive or negative according to the user's specification.

The target word is repeatedly played and the child made to choose numerous times in order to produce an estimate of the "percent correct" that is then recorded 160.

Choosing from a selection of target picture choices and being required to select from among them, makes the speech intelligibility test interactive for the child and more engaging. In addition, this 'closed set' format establishes a minimum level at which some success may be achieved by chance. For instance, in a 4-alternative-forced-choice paradigm, if the subject is guessing, approximately 25% of the trials are expected to be correct based on probability theory. The greater the number of choices, the lower the probability that the child is guessing, which increases the probability that what is being measured is speech intelligibility as opposed to some other process such as discrimination. The positive reinforcement animations also help to make the test more fun and enable the user to retain the child's attention for a longer period of time.

Presenting competing sounds 150. The target word may be presented to the child in silence or in the presence of one or more of the competing sounds. A user may opt to present a certain type of competing sound simultaneously with the target word and record the child's choice. As mentioned previously, the competing sounds may be presented in several different types.

The competing sounds may also be presented from a variety of locations relative to the target sound and to the child, thus enabling the testing of not only how the competing sound may mask a target word, but also whether and to what extent distancing the competing sound from the target sound eliminates its masking effect (i.e. the extent to which spatial release from masking occurs). One of the leading questions today involves the problem of listening in noise and reducing interference from competing sounds. In order to identify optimal conditions for this "noise reduction", speech intelligibility is measured in the presence of simulated competitor sound(s) that are either spatially coincident with the target word sound or spatially separated from it. The results may be used; understanding how a child's classroom environment, for example, may be modified to optimize the child's speech intelligibility. Where a child sits, may determine whether he or she can hear and understand what the teacher says, as may the particular settings on the child's amplification device (e.g. hearing aid, cochlear implant).

In any case, if a user wishes to test a child's hearing in the presence of competing sounds, the user sets the sound level for the competing sound, selects the competing sound and repeats the testing procedure (see FIG. 1). The user may also specify from what location the competing sound should be presented and whether more than one competing sound should be presented at the same time.

The presentations of target word and competing sounds (140–150), generally occurs in a room that is soundproof. However, a room may be customized to reverberate at a specified frequency in order to test those effects on the ability of the child to hear.

Adapting sound level given child's response 170. The method may optionally also comprise adapting the sound level at which the target word is presented according to the child's responses. Changing the sound level generally comprises determining a direction and an amount of an initial step size by which to change the sound level so as to adapt the change in current sound level to the child's response, the determination being governed by the set of rules (a so-called adaptive algorithm). The particular set of rules may vary with the user. An example of one such set of rules is given in FIG. 2. Employing this particular set of rules enables the speech intelligibility test to be administered quickly while still gaining reliable results. This is of particular benefit with children who typically have short attention spans.

Figure 2:
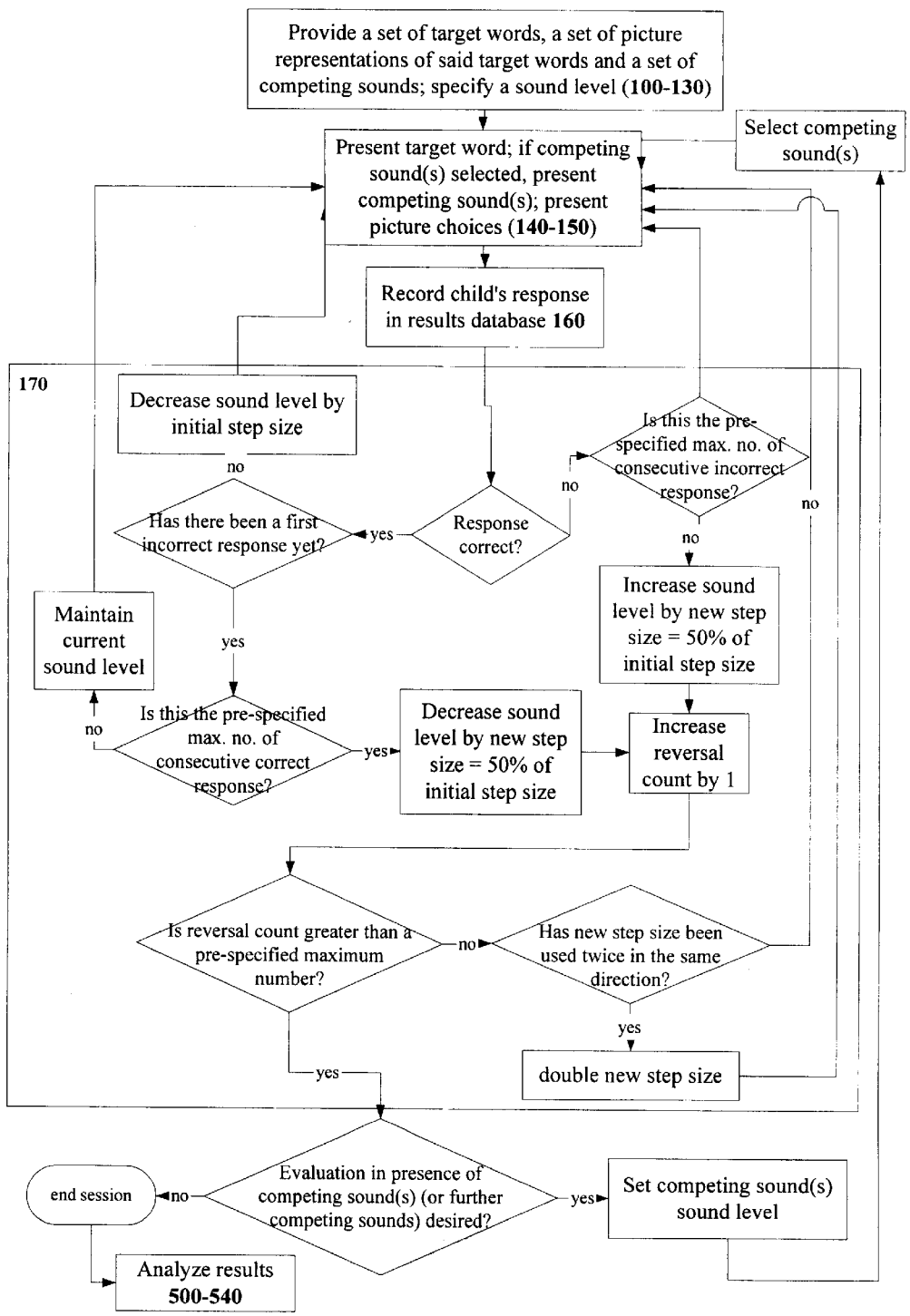
FIG. 2 shows a schematic diagram depicting steps in a version of the method that includes adapting sound level according to a set of rules in accordance to a child's responses.

Referring to FIG. 2, the example provided of a set of rules is depicted in the step 170 box. In summary, they are as follows:

(a) if the child's response is incorrect and if a number of consecutive incorrect responses is less than a pre-specified maximum number, then increasing the current sound level by a step size equal to one-half of the initial step size, else, re-setting the sound level to the sound level first specified;

(b) if the response is correct and there have been no previous incorrect responses, then decreasing the current sound level by the initial step size amount; else, (1) if a number of consecutive correct responses is less than a pre-specified maximum number, then not changing the current sound level, else, decreasing the sound level by a step size amount equal to one half of the initial step size;

(c) if the sound level has been changed in a particular direction by the set of rules and the step size by which the sound level has been changed is of a value that has been used twice consecutively in the same direction, then the step size by which the current sound level is changed is doubled; and, (d) if an end condition is not met, then repeating the steps from the presenting one of the target words step, else end repeating.

The rules may further specify counting a number of sound level reversals, a sound level reversal being a change in the direction of the sound level when the change is in an opposite direction from a previous sound level change. If so, the end condition may comprise a maximum allowable number of sound level reversals.

At completion of the speech intelligibility test, the child's responses are stored in a results database 490 to use in analyzing the effects of the type and location of competing sound(s) on the ability of the child to hear a target word. Users 520 may query 540 the results database 490 to produce a variety of output analyses 500 (see FIG. 4).

Detailed Description—System

The reader should note that, though the following description recites structures used in the system of the present invention and examples thereof when possible, applicant intends to encompass within the language any structure presently existing or developed in the future that performs the same function.

Figure 3:
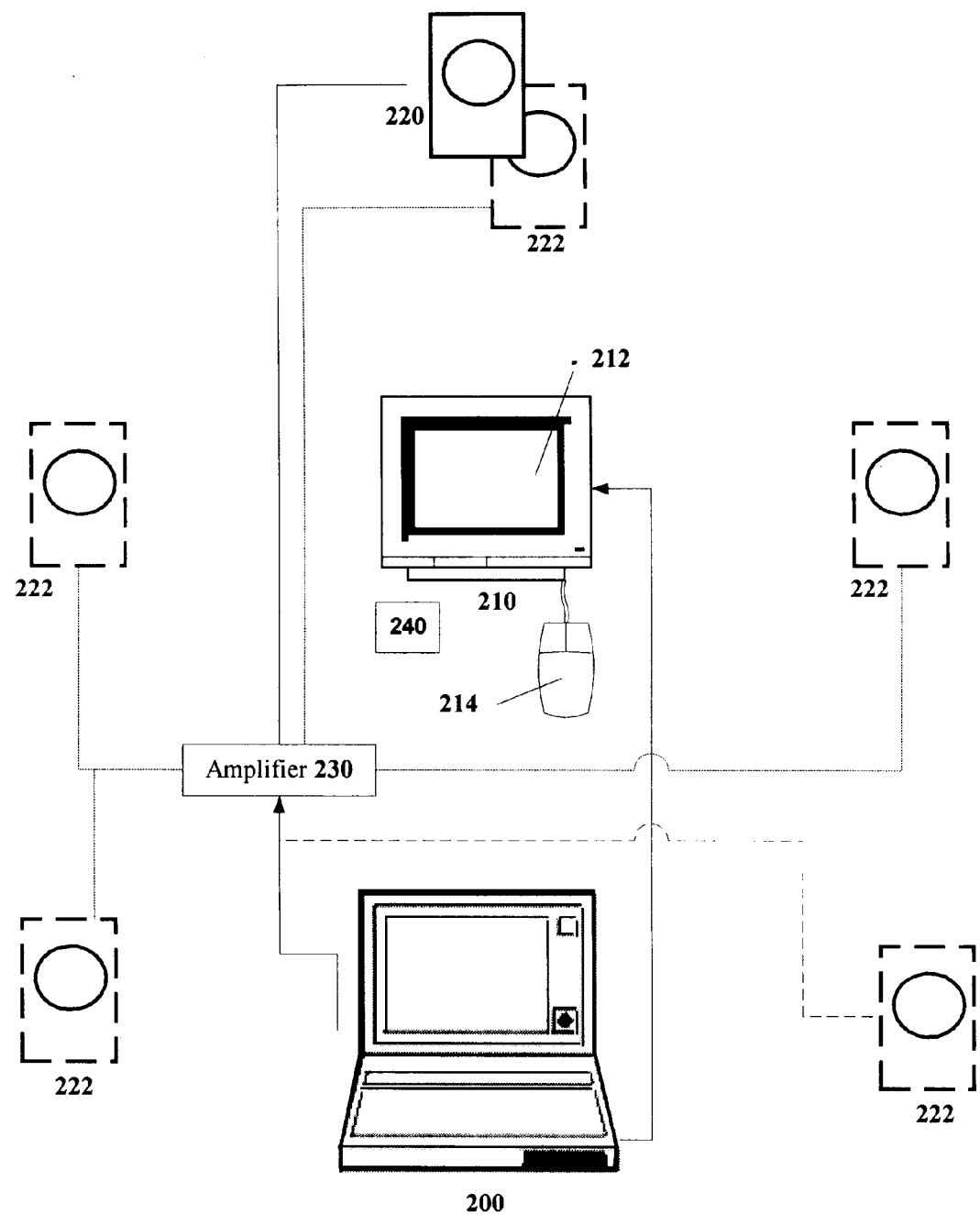
FIG. 3 shows a depiction of a version of a user and a subject station clinical setup; and, FIG. 4 shows a version of the system of the present invention.

Referring to FIG. 3, a typical situation is depicted for testing the speech intelligibility of a child. A user station 200 generally comprises a general-purpose computer, its component devices and software, that provide means for implementing the method steps described above. Further components of the system include a subject's station 210 at which the child sits, comprising a device connected to and controlled by the user's general-purpose computer at which the picture representations of words may be presented and with which the child may make selections. For example, the subject's station 210 may be a typical workstation at which the pictures may be presented on the screen 212 of a computer monitor or other similar device. The child may indicate his or her selections using a mouse 214 by positioning a cursor on the screen and clicking the mouse, or touching the screen (in the case of a touch-screen device), or by any similar means. Alternatively, the subject's station 210 may simply consist of a desk at which the child is presented with picture choices in hard-copy format such as in a book.

The system may further include an audio speaker 220 for use in presenting the target word and one or more other speakers 222 for presenting one or more of the competing sounds (see FIG. 3). The speakers (220 and 222) are controlled by the general-purpose computer 200 via an amplifier 230. Alternatively, the audio speakers (220, 222) may be replaced by headphones over which the target and competing sound(s) are presented to the child.

A measuring device such as a sound meter 240 for measuring the sound level (in decibels) of the target word in the proximity of the child's head, may also be included.

Figure 4:
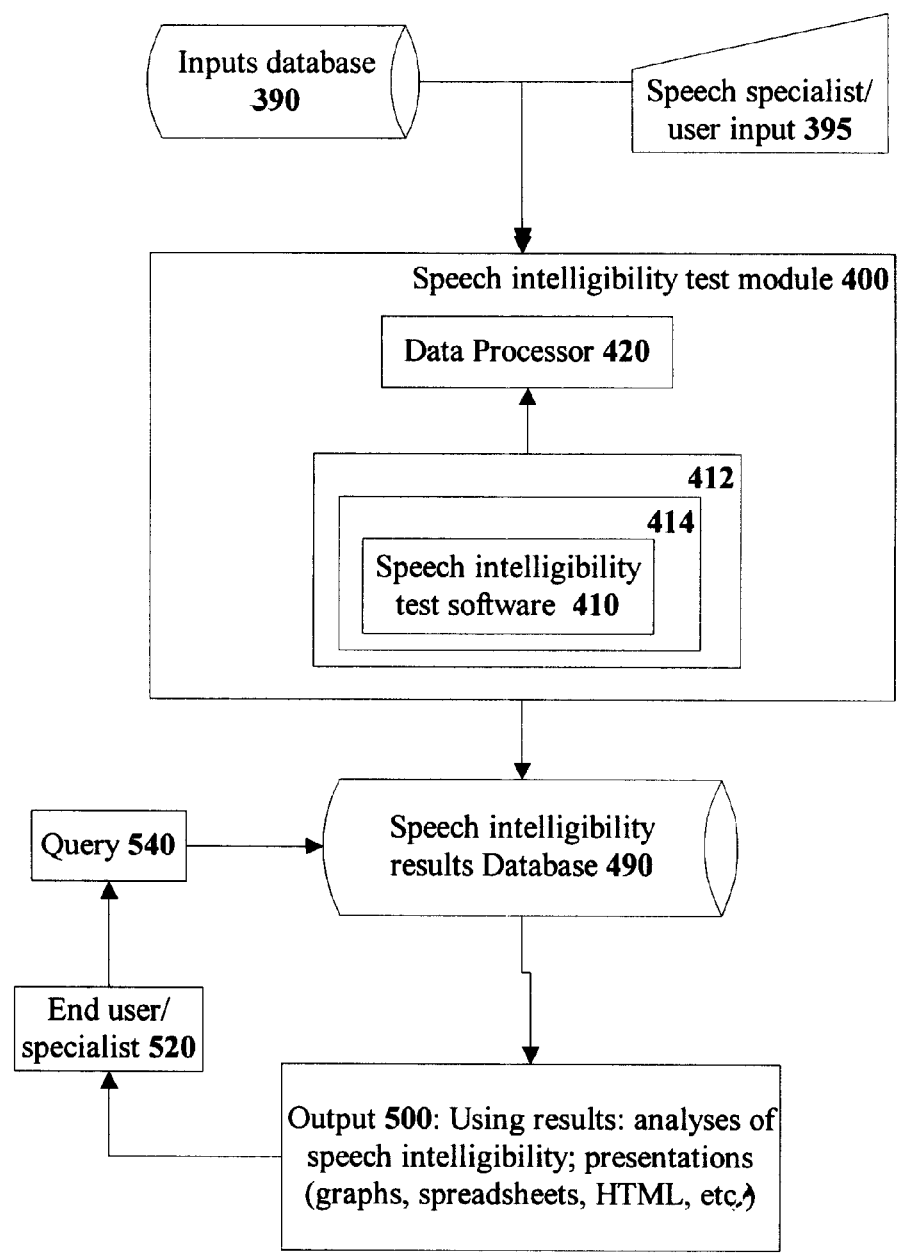

Referring to FIG. 4, a computer system of the present invention is depicted. A speech intelligibility test module 400 receives input from an inputs database 390 and a hearing expert or analyst 395. The inputs database 390 contains a variety of inputs to the speech intelligibility test program module 400, such as target word sound files, competing sounds sound files, target word picture representation graphics files, and the like. The inputs database 390 may be stored on the hard disk of the general-purpose computer 200, or may be provided on one or more storage devices such as a conventional disk, tape, or the like. Likewise the specialist/user may provide inputs 395 manually, or stored on a conventional storage device such as a disk, tape or the like.

The speech intelligibility test software 410 resides on a program storage device 412 having a computer usable medium 414 for storing the program code. The program storage device 412 may be of a conventional variety, such as a conventional disk or memory device. The speech intelligibility test software 410 may be created using general-purpose application development tools such as programming languages, graphical design tools, and commercially available reusable software components. A general database engine may be used to manage inputs data storage and retrieval. The processor 420 is part of the general-purpose computer system of the user station 300. Any general-purpose computer may be used, provided that the processing power is sufficient to achieve the desired speed of computation for the amount of inputs data being processed by the system.

Once the speech intelligibility test results are stored in the results database 490, they may be used in analyzing the effect(s) of type and location of competing sounds relative to the target and to the child, on the ability of the child to hear and/or understand the target word. The results database 490 may be queried by an end user 520 who can request specific information from the system through a query 540 and thereby produce customized output 500. The system accommodates post-processing of the output data 500, allowing delivery in various formats and through various electronic media. The system can generate output 500 in the form of further analyses and presentation as graphs, spreadsheets, HTML documents, or other formats. Queries 540 may be formulated to a user's specifications in order to create customized output to use in making treatment decisions to improve the child's speech intelligibility such as whether a hearing aid or cochlear implant would benefit the child more, which settings in the hearing aid or cochlear implant are most appropriate, and where a child might be positioned in a classroom to optimize their ability to hear a teacher. The output 500 can be delivered electronically through a variety of channels, including facsimile, e-mail, local area networks (LANs), wide area networks (WANs) and the worldwide web. It can also, of course, be provided in hard copy.

Of particular interest to audiology specialists, the results database 490 itself, or customized output data 500, may be incorporated into the specialist's information management system for intra-net online access (via a LAN or WAN) to enable service-wide access to results to enable specialists in the system to better understand the demographics of auditory impairments or other purposes. A particular specialist may also supply inputs to the system 395 (e.g., a particular set of target words to use or type of words to use, a starting sound level, a rules set for sound level variation, a protocol for presenting competing sounds including what types to present and where to locate them, specifications as to whether and at what extent to provide room reverberations, etc.) via the intra-net information system. In this way, the system of the present invention may be fully incorporated into a specialist's information system to provide a seamless interface to their audiology care database.

How the Invention is Used

In one version of the method and system of the present invention, the general-purpose computer 200 at the user station is programmed to display a user interface that enables the user administering the test to input certain parameters and/or modify those already set 395 (FIG. 4). The version described below is by way of example only, as the reader will understand that the particular computer user interface and/or steps of use may vary according to the needs of the particular user. It presents an example of how one might use the general-purpose computer 200 programmed to perform the steps in the method of the present invention to test a child subject. "The speech intelligibility program" refers to the methodology programmed to run on the general-purpose computer 200.

The speech intelligibility program may be opened by the user by clicking on an icon available on the desktop. Upon opening, the program looks for files containing the following: (a) "target" words; (b) "competing" sounds; (c) image files that match the target sounds (i.e. the picture representations of the target words); (d) animation files to be used for "positive feedback;" and, (e) sound files to be used for "negative feedback" (i.e. incorrect responses) (from inputs database 390). Depending on which speech test materials are employed, the user can upload particular files containing appropriate materials (i.e. from the inputs database 390 and/or provided by the user 395). The sound and image files that are used for the target word sounds and picture word presentations will generally be provided in pairs having the same name but ending with the suffix *.wav and *.jpg, respectively. For example, for a target word "airplane" there may be a sound file in which the word "airplane" is spoken, named 'airplane.wav', and a graphics file containing a picture of an airplane, named 'airplane.jpg'. The voice and graphics files may alternatively be provided in other text or graphics formats.

Upon initiation, the user interface may display several options that may be initiated by the user by clicking on their buttons, including for example, 'Start New Test,' 'Preferences,' 'Subjects Files,' 'Calibrate,' and 'Exit.'

The 'Start New Test' button option must be activated before any other options can be changed or applied. When the button is depressed, a screen including subject information and test settings is displayed. An output name for the unique data file that the test run will generate is entered into the Subject information 'name' box, followed by the date of testing in the 'date' box. A box for comments is also provided. Two or more audio speaker channels may be used by the program, one for controlling the presentation of target words at the target speaker 220, and one or more others for the competing sound speaker(s) 222 at which the competing sounds may be presented. Radio buttons allow the user to select from what audio speaker(s) the sounds are presented. A drop down list of competitor sounds is provided to select the type of competitor sound that will be presented in the second or other audio channel.

The signals generated by the computer are calibrated in order to "map out" the output levels of a sound card. Calibration is conducted without the subject in place. A sound level meter (SLM, 240) is held with its receiving microphone placed at the estimated position of the center of the subject's head. The user begins calibration by clicking on the 'Calibrate' button option. This displays a calibration screen with several options.

The 'Target sounds' radio button, for example, is chosen in order to calibrate the target word sounds. Words that have been loaded into the "target word list" (see below) are used by the calibration program. These words may be selected by the user prior to calibration. The user then clicks on a bar labeled 'Press me to start calibration' in order for the target words to be presented. While the words are being presented, the user notes the readings of the SLM and takes a running average of the peak amplitude. Once the user is confident of the estimated sound pressure level, the average reading from the SLM is entered in the available box and the 'OK' button is clicked.

To calibrate a competitor sound, the user clicks on the 'Competitor sound' radio button. The user must select which competing sound type should be calibrated from the drop-down list. The available sound type options may include (a) speech, (b) speech-shaped noise (containing the same long-term spectrum of the speech), (c) backward speech (i.e., tune-reversed speech; the same speech segment reversed in time (d) modulated speech shaped noise (MSSN; containing the same long-term spectrum of the speech and the same temporal envelope of the speech), (e) two simultaneous speech segments, (f) two simultaneous MSSN segments, and/or (g) other user-defined sound types. Once the competing sound type has been selected, the user clicks on a bar labeled 'Press me to start calibration' to begin presentation of the competitor sound. The readings on the SLM are observed for at least 10 seconds. Once the user is confident that the sound pressure level has been estimated, the button labeled 'stop' is pressed to end the sound presentation. The average reading from the SLM is entered in the available box.

There may be an option to check the accuracy of the calibration by selecting either the target or the competitor sound, selecting a desired level for the sound to be played, pressing the button labeled 'Play,' and taking an average reading from the SLM.

When the calibration seems satisfactory, the user clicks on the button labeled 'APPLY' in order to apply the calibration settings to the testing part of the program. Note that the level at which the target words and competitor sounds are calibrated is the maximum level that the program is able to use for that test run. Hence, the user must make sure to calibrate at the highest level that is anticipated for the test. If the highest level was underestimated, the calibration process can be repeated and new values stored. These values are stored as the default values the next time that the program is activated.

The user may modify the speech intelligibility test in any of several ways by selecting the 'Preferences' button option and providing particular inputs 395. This displays a new screen with multiple main sections where preferences may be specified. The output folder for the data file generated by the test run can be specified in the 'output folder' section of the screen. The 'animations' section of the screen controls which animated cartoons are used by the program as reinforcers. Using the buttons below, these cartoons can be previewed, added, or removed from the program.

The 'targets count' section of the screen controls which target words and corresponding pictures are presented during the test run. A default list of target words is automatically loaded. Buttons allow the user to create a new target word list, to save that list under a new file name, or to load a previously customized and saved target word list. Each target word and picture in the list can be previewed with the 'preview' button. In order to further customize a target list for a subject as he/she grows more familiar with the vocabulary, 'add item' and 'remove item' buttons exist. In the case of a user mistake, the 'empty current list' button can be depressed to clear target information and begin again.

A 'miscellaneous settings' section of the screen provides three preference options. The 'games settings' button allows the user to select specific picture files for use with the puzzle and fun paint programs. These are initiated after a test run is completed and allow the subject to participate in a relaxing, fan task before beginning another test run. The 'animations tuning' button will allow for changes in the way the animations files perform. There is a 'sound card enumeration' button for specifying the computer sound card device; by adding more sound cards to the computer one can potentially activate more than two channels at once.

After calibration and preferences have been set, the speech intelligibility program test run can be started. This is done on the 'Start New Test' screen. The test settings are specified in the 'Initial Test Settings' section of the screen. These settings correspond to some of the rules in a rules set (e.g. adaptive algorithm, see FIG. 2) that the program may optionally use to vary the target sound level during the test. The volume level in decibels (dB SPL) can be set for the competitor sound as well as for the initial presentation of the target word. The initial sound level decrease that the program may apply to a correctly identified target word may be specified. The number of reversals in direction of sound level change needed to end the test run as well as how many of those reversal levels to use in calculating a threshold number may also be specified. Finally, a feedback mode for incorrect answers may be chosen from among options including no feedback, negative, or positive feedback.

The speech intelligibility test program measures a speech intelligibility, a measurement that requires that the subject be familiar with each target word presented. A procedure for familiarizing the subject is included with the program and ensures that only target words within the vocabulary of the subject are used. It is initiated by clicking the 'Run familiarization' button on the 'Start New Test' screen.

The familiarization procedure uses words that have been loaded into the target word list and presents them one at a time, in the order that they are listed. During the familiarization process, a picture appears on the screen, the user depresses the 'Play Sound' button to activate the sound presentation corresponding to the picture displayed. There is also a slide bar that can be used to control the volume of the sound presentation. The word may be presented as many times as the user wishes. When the user is ready to move to the next target word, the 'Next' button is depressed.

After all target words have been displayed, the familiarization procedure brings up a message box which says, "To check how well child knows pictures press OK." Clicking OK begins the second display of the target pictures, one at a time, this time with no sound presentation options. The subject is to recite the word corresponding to the picture. The user enters "c" for correct and "i" for incorrect recitations.

When the subject has given a response for each of the pictures, the familiarization procedure brings up another message box that says, "Child knows 'N' pictures. Would you like to run familiarization again?" with the number of correct recitations entered in the 'N' space. The user can choose the "yes" option if the subject needs further training, or can choose the "no" option to proceed with testing. If "no" is chosen, there is an additional message box which asks, "Use these pictures in the test?" If "yes" is chosen, only those words the subject correctly recited will be loaded into the target list and presented during the test run. If "no" is chosen, all words from the initial default loaded list will be presented.

The program automatically displays the 'Start New Test' screen after the familiarization procedure finishes.

The speech intelligibility program test run begins by clicking on the 'Start Test' button at the bottom right corner of the 'Start New Test' screen. The first screen displayed is a preparation screen. On the left side of the screen, the trial number, target presentation level, step size and number of reversals is displayed for user information. In the middle of the screen is a large button with a picture of a traffic light on green and the word go. This button allows the user to make sure that the subject is in ready position and is pressed to begin target presentation.

When the 'go' button is pressed, the screen clears and the trial begins. In the 'Quiet' condition, the subject is simply instructed to pay attention to the front target loudspeaker 220 and to keep his/her head still and oriented towards the front.

In the 'Competitor' conditions, the subject is also instructed to ignore the 'competing sound' (being presented from one or more competitor speakers 222) and to pay attention to the target sound. If the competing sound is a female voice and the target a male voice, the instruction can simply be to "ignore the female voice and pay attention to the male voice," for example. The competitor sound (if one was selected) may play from one speaker 222. From the target speaker 220, a carrier phrase such as "Ready, point to the," is presented, followed by one of the target words. The user can choose which carrier phrase is presented by inserting an audio file containing that phrase in a specified directory on the computer. If no competitor sound is selected (Quiet condition), the trial proceeds in the same manner, except that the target word is played in isolation.

Once the target word has been presented, the speech intelligibility program then places multiple picture options (including the one corresponding to the target word chosen) on the screen display. The non-target word options are chosen at random from the target word list. The subject is asked to use the mouse to click on the picture of the word he or she heard. The subject is given feedback following the trial based on his or her response. If the response is correct, a musical cartoon animation may appear on the screen for about five seconds. If the response is incorrect, the feedback option chosen on the 'Start New Test' screen is implemented. For example, if no feedback was chosen, the 'go' button and the preparation screen immediately appear. If negative feedback was chosen, a phrase indicating that the response was incorrect is played from the loudspeaker (e.g., "That must have been difficult" or "Let's try another one"). If positive feedback was chosen, the musical cartoon animation appears just as for a correct response.

Following the feedback, the speech intelligibility program advances to the next trial and displays the preparation screen. The target presentation level for the trial may be "adaptive" in that it is determined according to the subject's performance as specified by the adaptive algorithm (see methods description above, FIG. 2). For example, initially, for a correct response, the sound level is decreased by the step size specified in the preferences menu (default is 8 dB) until an incorrect response is given. At that point, the level is increased by half of the level used in the initial step. At this point, an adaptive rule is activated. A pre-specified maximum number of correct responses must occur in a row in order for the level to be decreased; but following each incorrect response the level is increased.

The test run finishes after the level has been increased and decreased (reversed direction) the number of times specified in the 'Start New Test' screen. At that time, the program creates a data file (name specified earlier; the hearing results database 490) which stores information regarding the test conditions, target words presentation levels for each trial, levels corresponding to the reversals, and a threshold calculation. This data file may be stored in text (ASCII) or other formats.

If difficulties are encountered during the test run, several options exist which require that the user depress the Escape key on the computer keyboard. This activates a message with the option to 'Abort' end the test run, to 'Retry' repeat just the previous trial, or to 'Ignore' and advance to the next trial.

Finally, once the data file has been stored, the program offers the subject the option of a puzzle or fun paint picture. The user 520 may access the results in the results database 490 to create further output 500 by querying 540 the database 490. For example, the speech reception of the child as a function of type of competing sound, the degree to which spatial release from masking occurs as a function of location of the competing sound, or other analyses.

Advantages of the Invention

The previously described versions of the present invention have many advantages, including providing:

a) a method and system for clinically testing speech intelligibility of children in such as way as to link the child's normal environmental noise experience to the audiology clinic;

b) a rapid and reliable method and system for testing the speech intelligibility of a child that is adapted to engage children so as to enable a tester to determine what auditory factors are contributing to the child's speech intelligibility level;

c) a method and system for simulating a child's normal classroom environment by providing a variety of types of competing noises so as to determine their effect(s) on the speech intelligibility of the child;

d) a method and system for testing the effects of location of competing noises relative to a target word source and the child so as to determine the spatial release from masking potential of said location; and, e) system for computerizing the method so as to enable a clinical user to more accurately control the presentation of sounds, the storage and analysis of results, and by which the child may interactively make choices and receive reinforcement.

The present invention does not require that all the advantageous features and all the advantages need to be incorporated into every embodiment thereof.

Closing

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A method for testing speech intelligibility of a child, comprising:

providing a set of target words for presenting to the child from an auditory target located in front of and at a distance from the child;

providing a set of picture representations of each of said target words for visually presenting to the child;

providing a set of competing sounds of an at least one type selected from the group consisting of speech, speech-shaped noise, time-reversed speech and temporally modulated speech-shaped noise;

selecting an at least one type of competing sound from the set provided to use in testing;

specifying a sound level at which a target word is presented so as to ensure hearing by the child in the absence of any of the competing sounds;

presenting one of the target words to the child at the sound level;

presenting a subset of the picture representations to the child of which one matches the presented target word, the child then responding to the presentation by choosing which of the subset of pictures matches the target word, and recording the child's response;

repeating the presenting the target word step while furthermore simultaneously presenting one of the at least one selected type(s) of the competing sounds at a location proximate the target and repeating the presenting the picture representations step, over all of the at least one type of competing sounds selected; and, repeating the presenting the target word step while furthermore simultaneously presenting one of the at least one selected type(s) of competing sounds at a location at a distance away from both the target and the child and repeating the presenting the picture representations step, over all of the at least one type of competing sounds selected;

whereby the child's responses are recorded to use in measuring an interference and masking effect of the competing sound by its type and location on an ability of the child to hear the target and to spatially segregate sounds using binaural hearing, that is, the degree to which masking and spatial release from masking can occur given characteristics of the type of competing sound and its location relative to the child and to the target, the measurements informing treatment options to improve the child's speech intelligibility in realistic complex environments.

2. The method of claim 1, further comprising calibrating the sound level of the target word at a site of location of the child's head.

3. The method of claim 1, wherein the set of competing sounds further comprises a user-specified sound.

4. The method of claim 1, wherein the at least one competing sound comprises two competing sounds simultaneously presented at two different locations relative to the target and the child.

5. The method of claim 1, further comprising changing the sound level at which the target word is presented according to the child's response.

6. The method of claim 5, wherein changing the sound level comprises determining a direction and an amount of an initial step size by which to change the sound level so as to adapt the change in current sound level to the child's response, the determination being governed by a set of rules.

7. The method of claim 6, wherein the set of rules comprises:

if the response is incorrect and if a number of consecutive incorrect responses is less than a pre-specified maximum number, then increasing the current sound level by a step size equal to one-half of the initial step size, else, re-setting the sound level to the sound level first specified;

if the response is correct and there have been no previous incorrect responses, then decreasing the current sound level by the initial step size amount; else, if a number of consecutive correct responses is less than a pre-specified maximum number, then not changing the current sound level, else, decreasing the sound level by a step size amount equal to one half of the initial step size;

if the sound level has been changed in a particular direction by the set of rules and the step size by which the sound level has been changed is of a value that has been used twice consecutively in the same direction, then the step size by which the current sound level is changed is doubled; and, if an end condition is not met, then repeating the steps from the presenting one of the target words step, else end repeating.

8. The method of claim 7, further comprising counting a number of sound level reversals, a sound level reversal comprising a change in the direction of the sound level when the change is in an opposite direction from a previous sound level change.

9. The method of claim 8, wherein the end condition comprises a maximum allowable number of sound level reversals.

10. An apparatus for testing speech intelligibility of a child, comprising:

means for providing a set of target words for presenting to the child from an auditory target located in front of and at a distance from the child;

means for providing a set of picture representations of each of said target words for visually presenting to the child;

means for providing a set of competing sounds of an at least one type selected from the group consisting of speech, speech-shaped noise, time-reversed speech and temporally modulated speech-shaped noise;

means for selecting an at least one type of competing sound from the, set provided to use in testing;

means for specifying a sound level at which a target word is presented so as to ensure hearing by the child in the absence of any of the competing sounds;

means for presenting one of the target words to the child at the sound level;

means for presenting a subset of the picture representations to the child of which one matches the presented target word, the child then responding to the presentation by choosing which of the subset of pictures matches the target word, and recording the child's response;

means for changing the sound level at which the target word is presented according to the child's response and repeating the presenting the target word step, changing the sound level comprising determining a direction and an amount of an initial step size by which to change the sound level so as to adapt the change in current sound level to the child's response, the determination being governed by a set of rules;

means for repeating the presenting the target word step while furthermore simultaneously presenting one of the at least one selected type(s) of the competing sounds at a location proximate the target and repeating the presenting the picture representations step, over all of the at least one type of competing sounds selected; and, means for repeating the presenting the target word step while furthermore simultaneously presenting one of the at least one selected type(s) of competing sounds at a location at a distance away from both the target and the child and repeating the presenting the picture representations step, over all of the at least one type of competing sounds selected;

whereby the child's responses are recorded to use in measuring an interference and masking effect of the competing sound by its type and location on an ability of the child to hear the target and to spatially segregate sounds using binaural hearing, that is, the degree to which masking and spatial release from masking occur given characteristics of the type of competing sound and its location relative to the child and to the target, the measurements informing treatment options to improve the child's speech intelligibility in realistic complex environments.

11. The apparatus of claim 10, further comprising means for calibrating the sound level of the target word at a site of location of the child' head.

12. A program storage device readable by a machine tangibly embodying a program of instructions executable by the machine to perform method steps for testing speech intelligibility of a child, the method steps comprising:

providing a set of target words for presenting to the child from an auditory target located in front of and at a distance from the child;

providing a set of picture representations of each of said target words for visually presenting to the child;

providing a set of competing sounds of an at least one type selected from the group consisting of speech, speech-shaped noise, time-reversed speech and temporally modulated speech-shaped noise;

selecting an at least one type of competing sound from the set provided to use in testing;

specifying a sound level at which a target word is presented so as to ensure hearing by the child in the absence of any of the competing sounds;

presenting one of the target words to the child at the sound level;

presenting a subset of the picture representations to the child of which one matches the presented target word, the child then responding to the presentation by choosing which of the subset of pictures matches the target word, and recording the child's response;

changing the sound level at which the target word is presented according to the child's response and repeating the presenting the target word step, changing the sound level comprising determining a direction and an amount of an initial step size by which to change the sound level so as to adapt the change in current sound level to the child's response, the determination being governed by a set of rules;

repeating the presenting the target word step while furthermore simultaneously presenting one of the at least one selected type(s) of the competing sounds at a location proximate the target and repeating the presenting the picture representations step, over all of the at least one type of competing sounds selected; and, repeating the presenting the target word step while furthermore simultaneously presenting one of the at least one selected type(s) of competing sounds at a location at a distance away from both the target and the child and repeating the presenting the picture representations step, over all of the at least one type of competing sounds selected;

whereby the child's responses are recorded to use in measuring an interference and masking effect of the competing sound by its type and location on an ability of the child to hear the target and to spatially segregate sounds using binaural hearing, that is, the degree to which masking and spatial release from masking occur given characteristics of the type of competing sound and its location relative to the child and to the target, the measurements informing treatment options to improve the child's speech intelligibility in realistic complex environments.

13. An article of manufacture comprising a computer-usable medium having computer-readable program code means embodied in said medium for testing speech intelligibility of a child, said computer-readable program code means comprising:

program code means for providing a set of target words for presenting to the child from an auditory target located in front of and at a distance from the child;

program code means for providing a set of picture representations of each of said target words for visually presenting to the child;

program code means for providing a set of competing sounds of an at least one type selected from the group consisting of speech, speech-shaped noise, time-reversed speech and temporally modulated speech-shaped noise;

program code means for selecting an at least one type of competing sound from the set provided to use in testing;

program code means for specifying a sound level at which a target word is presented so as to ensure hearing by the child in the absence of any of the competing sounds;

program code means for presenting one of the target words to the child at the sound level;

program code means for presenting a subset of the picture representations to the child of which one matches the presented target word, the child then responding to the presentation by choosing which of the subset of pictures matches the target word, and recording the child's response; program code means for changing the sound level at which the target word is presented according to the child's response and repeating the presenting the target word step, changing the sound level comprising determining a direction and an amount of an initial step size by which to change the sound level so as to adapt the change in current sound level to the child's response, the determination being governed by a set of rules;

program code means for repeating the presenting the target word step while furthermore simultaneously presenting one of the at least one selected type(s) of the competing sounds at a location proximate the target and repeating the presenting the picture representations step, over all of the at least one type of competing sounds selected; and, program code means for repeating the presenting the target word step while furthermore simultaneously presenting one of the at least one selected type(s) of competing sounds at a location at a distance away from both the target and the child and repeating the presenting the picture representations step, over all of the at least one type of competing sounds selected;

whereby the child's responses are recorded to use in measuring an interference and masking effect of the competing sound by its type and location on an ability of the child to hear the target and to spatially segregate sounds using binaural hearing, that is, the degree to which masking and spatial release from masking occur given characteristics of the type of competing sound and its location relative to the child and to the target, the measurements informing treatment options to improve the child's speech intelligibility in realistic complex environments.

14. A computer program product comprising:

a computer usable medium and computer readable code embodied on said computer useable medium for causing the testing of speech intelligibility of a child, comprising:

computer readable program code devices configured to cause the computer to effect the providing of a set of target words for presenting to the child from an auditory target located in front of and at a distance from the child;

computer readable program code devices configured to cause the computer to effect the providing of a set of picture representations of each of said target words for visually presenting to the child;

computer readable program code devices configured to cause the computer to effect the providing of a set of competing sounds of an at least one type selected from the group consisting of speech, speech-shaped noise, time-reversed speech and temporally modulated speech-shaped noise;

computer readable program code devices configured to cause the selecting of an at least one type of competing sound from the set provided to use in testing;

computer readable program code devices configured to cause the computer to effect the specifying of a sound level at which a target word is presented so as to ensure hearing by the child in the absence of any of the competing sounds;

computer readable program code devices configured to cause the computer to effect the presenting of one of the target words to the child at the sound level;

computer readable program code devices configured to cause the computer to effect the presenting of a subset of the picture representations to the child of which one matches the presented target word, the child then responding to the presentation by choosing which of the subset of pictures matches the target word, and recording the child's response;

computer readable program code devices configured to cause the computer to effect the changing of the sound level at which the target word is presented according to the child's response and repeating the presenting the target word step, changing the sound level comprising determining a direction and an amount of an initial step size by which to change the sound level so as to adapt the change in current sound level to the child's response, the determination being governed by a set of rules;

computer readable program code devices configured to cause the computer to effect the repeating of the presenting the target word step while furthermore simultaneously presenting one of the at least one selected type(s) of the competing sounds at a location proximate the target and repeating the presenting the picture representations step, over all of the at least one type of competing sounds selected; and, computer readable program code devices configured to cause the computer to effect the repeating of the presenting the target word step while furthermore simultaneously presenting one of the at least one selected type(s) of competing sounds at a location at a distance away from both the target and the child and repeating the presenting the picture representations step, over all of the at least one type of competing sounds selected;

whereby the child's responses are recorded to use in measuring an interference and masking effect of the competing sound by its type and location on an ability of the child to hear the target and to spatially segregate sounds using binaural hearing, that is, the degree to which masking and spatial release from masking occur given characteristics of the type of competing sound and its location relative to the child and to the target, the measurements informing treatment options to improve the child's speech intelligibility in realistic complex environments.

15. A method for testing speech intelligibility of a child, comprising:

providing a set of target words for presenting to the child from an auditory target located in front of and at a distance from the child;

providing a set of picture representations of each of said target words for visually presenting to the child;

providing a set of competing sounds of an at least one type selected from the group consisting of speech, speech-shaped noise, time-reversed speech and temporally modulated speech-shaped noise;

selecting an at least one type of competing sound from the set provided to use in testing;

specifying a sound level at which a target word is presented so as to ensure hearing by the child in the absence of any of the competing sounds;

presenting one of the target words to the child at the sound level;

presenting a subset of the picture representations to the child of which one matches the presented target word, the child then responding to the presentation by choosing which of the subset of pictures matches the target word, and recording the child's response;

changing the sound level at which the target word is presented according to the child's response and repeating the presenting the target word step, changing the sound level comprising determining a direction and an amount of an initial step size by which to change the sound level so as to adapt the change in current sound level to the child's response, the determination being governed by a set of rules;

repeating the presenting the target word step while furthermore simultaneously presenting one of the at least one selected type(s) of the competing sounds at a location proximate the target and repeating the presenting the picture representations step, over all of the at least one type of competing sounds selected; and, repeating the presenting the target word step while furthermore simultaneously presenting one of the at least one selected type(s) of competing sounds at a location at a distance away from both the target and the child and repeating the presenting the picture representations step, over all of the at least one type of competing sounds selected;

whereby the child's responses are recorded to use in measuring an interference and masking effect of the competing sound by its type and location on an ability of the child to hear the target and to spatially segregate sounds using binaural hearing, that is, the degree to which masking and spatial release from masking occur given characteristics of the type of competing sound and its location relative to the child and to the target, the measurements informing treatment options to improve the child's speech intelligibility in realistic complex environments.

16. The method of claim 15, further comprising calibrating the sound level of the target word at a site of location of the child's head.

17. The method of claim 15, wherein the set of competing sounds further comprises a user-specified sound.

18. The method of claim 15, wherein the at least one competing sound comprises two competing sounds simultaneously presented at two different locations relative to the target and the child.

19. The method of claim 15, wherein the set of rules comprises:

if the response is incorrect and if a number of consecutive incorrect responses is less than a pre-specified maximum number, then increasing the current sound level by a step size equal to one-half of the initial step size, else, re-setting the sound level to the sound level first specified;

if the response is correct and there have been no previous incorrect responses, then decreasing the current sound level by the initial step size amount; else, if a number of consecutive correct responses is less than a pre-specified maximum number, then not changing the current sound level, else, decreasing the sound level by a step size amount equal to one half of the initial step size;

if the sound level has been changed in a particular direction by the set of rules and the step size by which the sound level has been changed is of a value that has been used twice consecutively in the same direction, then the step size by which the current sound level is changed is doubled; and, if an end condition is not met, then repeating the steps from the presenting one of the target words step, else end repeating.

20. The method of claim 19, further comprising counting a number of sound level reversals, a sound level reversal comprising a change in the direction of the sound level when the change is in an opposite direction from a previous sound level change.

21. The method of claim 20, wherein the end condition comprises a maximum allowable number of sound level reversals.

* * * * *